(12) United States Patent
Kerr et al.

(10) Patent No.: US 9,603,698 B2
(45) Date of Patent: Mar. 28, 2017

(54) BIOCOMPATIBLE MESH IMPLANT

(71) Applicants: Marshall Kerr, Carlsbad, CA (US);
Donn K. Harms, Del Mar, CA (US)

(72) Inventors: Marshall Kerr, Carlsbad, CA (US);
Donn K. Harms, Del Mar, CA (US)

(*) Notice: Subject to any disclaimer, the term of this patent is extended or adjusted under 35 U.S.C. 154(b) by 2 days.

(21) Appl. No.: 13/850,987

(22) Filed: Mar. 26, 2013

(65) Prior Publication Data

US 2013/0253645 A1 Sep. 26, 2013

Related U.S. Application Data

(60) Provisional application No. 61/615,523, filed on Mar. 26, 2012.

(51) Int. Cl.
*A61F 2/12* (2006.01)
*A61F 2/00* (2006.01)

(52) U.S. Cl.
CPC .............. *A61F 2/12* (2013.01); *A61F 2/0063* (2013.01); *A61F 2250/0097* (2013.01)

(58) Field of Classification Search
CPC ........ A61F 2/12; A61F 2/0063; A61F 2/0045; A61F 2250/0097
USPC ......................................... 623/7–8
See application file for complete search history.

(56) References Cited

U.S. PATENT DOCUMENTS

| | | | |
|---|---|---|---|
| 5,584,884 A * | 12/1996 | Pignataro ........................... 623/8 |
| 8,480,557 B2 * | 7/2013 | Guterman ....................... 600/37 |
| 2007/0123915 A1 * | 5/2007 | Kammerer ............ A61F 2/0045 606/151 |
| 2008/0027273 A1 * | 1/2008 | Gutterman ....................... 600/37 |
| 2008/0103351 A1 * | 5/2008 | Montpetit et al. ............... 600/30 |
| 2008/0215071 A1 * | 9/2008 | Zimmermann et al. ...... 606/151 |
| 2009/0069826 A1 * | 3/2009 | Walther et al. ............... 606/151 |
| 2009/0082864 A1 * | 3/2009 | Chen et al. ....................... 623/8 |
| 2010/0137679 A1 * | 6/2010 | Lashinski et al. .............. 600/37 |
| 2010/0331612 A1 * | 12/2010 | Lashinski et al. .............. 600/37 |
| 2011/0106249 A1 * | 5/2011 | Becker ............................... 623/8 |
| 2011/0224703 A1 * | 9/2011 | Mortarino ..................... 606/151 |
| 2012/0004723 A1 * | 1/2012 | Mortarino et al. ............... 623/8 |
| 2012/0221104 A1 * | 8/2012 | Altman et al. .................... 623/8 |
| 2013/0253646 A1 * | 9/2013 | Altman et al. .................... 623/8 |
| 2013/0281770 A1 * | 10/2013 | Alinsod ................ A61F 2/0045 600/37 |
| 2014/0046442 A1 * | 2/2014 | Guterman ......................... 623/8 |
| 2014/0074129 A1 * | 3/2014 | Walther et al. ............... 606/151 |
| 2014/0222146 A1 * | 8/2014 | Moses et al. ...................... 623/8 |
| 2015/0230913 A1 * | 8/2015 | Derwin ..................... A61F 2/02 623/23.72 |
| 2016/0310262 A1 * | 10/2016 | Doucet ..................... A61F 2/12 |

* cited by examiner

*Primary Examiner* — Suzette J Gherbi (74) *Attorney, Agent, or Firm* — Donn K. Harms (57) ABSTRACT

A mesh device for supporting one or a combination of a breast implant or breast tissue is provided formed of interlaced filaments forming a mesh structure which will not unravel when cut across a mid section of the mesh device. A titanium layer positioned on the exterior surface of the filaments of the mesh provide both a biocompatible interface with surrounding tissue and enhanced engagement of the filaments to prevent unraveling.

13 Claims, 3 Drawing Sheets

BIOCOMPATIBLE MESH IMPLANT

This application Claims Priority to U.S. Provisional Patent Application Ser. No. 61/615,523 filed on Mar. 26, 2012 and is included herein in its entirety by this reference thereto.

BACKGROUND OF THE INVENTION

1. Field of the Invention

The present invention relates generally to medical mesh implants conventionally used for tissue support and cell growth latices. More specifically, the device relates to a woven or warp knitted mesh implant device, having a bonding of titanium positioned to cover and provide an interface to the exposed fiber surfaces and contacting body tissue. So positioned, the titanium provides significantly enhanced bio-compatibility of the underlying fabric and device with the body in which it implants. The device is especially well adapted for employment in breast reconstructive surgery through the provisions of thread weaving, or especially knitting configurations, which provide a customized implant support structure in combination with bio-compatibility.

2. Prior Art

Breast cancer is one of the most common cancers among women. If the disease is not caught early, it is common that large portions of breast tissue are removed. In a conventional procedure called mastectomy, one or both breasts are partially or completely removed in order to treat or subsequently prevent breast cancer. Since such procedures generally result in a substantial amount of tissue being removed, many women will then opt for breast reconstructive surgery in order to reform the breast into a natural looking state. It is often acknowledged that the process of cancer treatment and removal of breast tissue can weigh heavily not only on the patients physical but also emotional well being. Thus, such surgery to reconstruct the breast can allow the patient to maintain self confidence after such an ordeal.

Many techniques of breast reconstruction and enhancement are known in the art. Such procedures generally involve employment of prosthetics, one's own body tissue, or a combination thereof, which are employed as implants for reforming the breast. Prosthetic implants are the most common technique known in the art and are used both for reconstructive and cosmetic surgery. This involves the employment of silicon, saline, or other suitable material formed implants, tissue expanders or the like, which are placed either below the muscle (submuscular) or above the muscle (subglandular) for forming and shaping the breast.

A first well known surgical method for breast reconstruction is transverse rectus abdominal muscle flap (or TRAM flap) surgery wherein a portion of abdominal tissue is employed to reconstruct the breast. The abdominal muscle is typically removed from the abdomen and then placed where the breast is to be formed. By employing ones own body tissue, the reconstructed site most often accepts the tissue and will limit further complication in that manner.

However, since initial removal of tissue from the abdomen is required, the procedure is time consuming, requires multiple surgeons and surgical sites, and may require long convalescence. In addition, the abdominal muscle may stay weakened and may further suffer from incisional hernias in the abdomen, thereby further prolonging recovery. Further, additional scars will typically be present and visible in the abdominal region at the site of tissue removal. As such, this type of surgery is typically considered a higher risk then prosthetic implant surgery.

Another example of body tissue breast formation is referred to as deep interior epigastric perforator (DIEP). This technique is also known to generally require multiple surgeons performing multiple incisions at different sites on the patient. In this procedure the surgeons harvest and employ abdominal tissue, however without muscle tissue, wherein only skin and blood vessels are transplanted. This method is often preferred over TRAM technique since muscle is not removed, and recovery can be shorter. However, this technique still suffers from some of the downfalls of the TRAM technique, including but not limited to, large amount of operating room and surgeon time, multiple surgeons, and surgical scars on multiple parts of the patients body.

Still another well known technique involves the transplant of skin and muscle from the back, namely the latissimus dorsi. Back muscles are generally thinner than the abdominal muscles, which allows surgeons to combine the muscle tissue with prosthetic implants such that the implant can maintain a more natural looking shape, volume, and feel. However, this technique again generally involves multiple surgeries and surgeons and is a time consuming surgery with a long post-operation recovery. Further, the removal of muscle tissue may result in the back muscle being weakened which can cause long term pain for the recovering patient. In addition, large scars will remain on the back and breast area.

While these and other techniques endeavor to minimize rejection issues by employing the patient's own body tissue for supporting existing breast tissue, or implanted prosthetics, this positive goal is generally negated by the fact that multiple surgeries and surgeons are required, and the fact that the patient has multiple incision sites and lost remote tissue that must heal and can become infected and painful. Consequently, a device and method which would provide customized support to the surgeon in their art to reshape the breast aesthetically, with minimized rejection and not requiring extra surgical procedures, would be of benefit to both patient and surgeon in such procedures.

As a conventional solution, the use of medical surgical mesh material as a support material is known in the art. One skilled in the art may immediately recognize many prior and related art provides surgical mesh devices, typically made from synthetic materials such as woven polypropylene or other synthetic and natural fabrics, which are implanted during all types of reconstructive or cosmetic surgery. Conventionally, the woven surgical mesh is provided as a flat substantially rectangular sheet which the physician must accurately cut to size in an attempt to fit the natural curvature of a breast as needed per patient for adequate support.

Unfortunately, the conventional woven mesh materials used today make no provision for accommodating stretch in one or both directions on a controlled basis. This is especially true with conventionally employed woven fabrics which generally provide no stretch or stretch in a single direction of the either the warp or the fill of the weave.

Because of this inability to customize elasticity and stretch to the mesh, these conventional devices may fail in providing adequate support and comfort in the natural movement and feel of the breast which for each human is of a custom dimension and area. This poor fit and lack of elasticity to allow for form fitting of the breast, may result in additional surgeries to correct such inconsistences. In addition, as has been discovered recently from long term implants, due to body reactions to some synthetic materials used for weaving such mesh devices, the mesh can be rejected by the patient's body even years after implantation. This rejection either evidenced immediately or over a term of years, can also be the causation of infection, damage to tissue, and again the need for subsequent surgeries to remove or replace the mesh device.

Further, currently provided to physicians for breast support are conventional square sheets of woven mesh fabric which are neither configured to size nor cut to shape to form the proper three dimensional shape when placed in a supportive engagement in an arc under the breast tissue or implants. As such, surgeons in the operating room, must take valuable time and cut the woven fabric sheet in the operating room during the procedure.

As such, this need for cutting woven mesh fabric, frequently results in uneven or miss-cut sheets of woven mesh which are then implanted and must be forcefully stretched or manipulated into a "fitted" engagement to the breast of the patient. To maintain this fitted engagement, the surgeon resorts to sutures or staples through the mesh and into surrounding tissue.

However, as noted, conventional mesh fabric being normally woven structures, are typically adapted to allow for partial stretch and only in one direction of either the warp thread running longwise or the fill thread running 90 degrees or perpendicular to the warp. Often the mesh structure will be positioned in the patient to permit stretch in the horizontal direction in an attempt to accommodate the volume of the breast, while resisting stretch in the vertical direction, in order to maintain support for breast tissue against the force of gravity on the implant or breast tissue. This results in an improper fit around the curved area of the breast tissue in the vertical direction which can be painful amongst other problems noted herein.

One skilled in the art will quickly ascertain that the dimensions and configurations of the mesh for each breast will vary widely for each instance of the procedure and the desired outcome of breast size, shape, and form. However, as a consequence of the lack of customized implant fabric sheets, which are knitted or woven and pre-cut to fit breast tissue, and the lack of predetermined stretch and support in both directions of supported breast tissue, can adversely effect the finished shape and feel of the reconstructed breast tissue. As such, patients will frequently suffer from discomfort from the material compressing the breast tissue, or from a distaste for the visual aspects of the finished surgery. Such patients will often require further surgeries to correct any inconsistencies with the mesh, or such patients may just unfortunately live with the uncomfortable current state of the reconstruction as well as the now known problems with fabric mesh rejection and infection.

Such surgical mesh is also known in the art to be employed in the abdominal region to prevent incisional hernias at the sites of muscle removal, and is commonly known for employment with other types of hernia repair. Some well known problems with conventional surgical mesh devices include high overall weight and stiffness and lack of three dimensional elasticity which is inherent to the typically rectangular woven mesh sheets. Further such mesh sheets used abdominally also have been found most recently to lack biocompatibility between the synthetic materials forming the sheets and contacting surrounding body tissue, thereby causing inflamation and in some cases illness and rejection.

When such surgical mesh is employed with breast reconstructive surgery, as noted, the stiffness and weave of such conventional mesh in one or both directions, can seriously inhibit the natural look, movement, and feel of the breast tissue and such is undesirable. Further, stiff or inelastic materials formed into woven structures can prove more difficult to handle by the physician during implantation due to the need to customize the planar non elastic sheet, to fit the curved three dimensional shape of a breast. Such misfitting sheets customized in the operating room frequently require suturing or stapling to maintain their position in the body.

As also noted, bio-compatibility and the possibility of the body's rejection of a fabric implant is a continuing problem with nearly all implant devices and most recently has been shown to be a particularly acute problem with woven fabric mesh. This lack of compatibility has been shown to be caused by the material forming the threads or yarn of the woven material.

A conventional solution is the use of known synthetic materials, such as polyanhydrides, which provide some bio-compatibility, in place of the conventional polypropylene or polystyrene or polyethylene yarns and threads used in mesh weaving. These materials may be provided in continuos unitary fibers, filaments, or strands of the material, which are sewn, woven as needed, to construct the planar mesh for implantation.

However, even such conventional thought to be bio-compatible synthetics, are still known to be subject to blood clot formation, infection, allergic reactions and more, and have been shown to be never completely bio-compatible. In addition, when employing such known bio-compatible synthetic or natural materials for forming into the yarn, fine fibers or filament strands which is then woven as needed, it has been found the strands in the weave may become brittle when formed into monofilament strands, and may incur some problems with stiffness and breakage.

Therefor, there is a need for a mesh implant device, able to employ known materials suitable for construction into a planar mesh structure, such as polypropylene or polystyrene or polyethylene, which is also biocompatible. Such a device should be able to employ conventional yarns for weaving or knitting to keep costs reasonable, but which also are provided an exterior surface layer, or coating, on the formed material or the yarn forming the material, which may then be employed for implantation and provide enhanced bio-compatibility. Thus, the provision of a bio-compatible surface layer or coating provided on the known textile yarns and strands suitable form forming into a mesh structure, should yield a finished mesh device which is adequately flexible and employs features of bio-compatibility.

Additionally, rather than forming the mesh using fabric weaving construction of warp and fill yarns or threads, which provide little elasticity except in directions normal to the two woven threads, the forming of implant fabric will be enhanced if knitted from the threads or yarns by the provision of two enhancements to implantation.

First, by knitting the mesh fabric, a three dimensional stretching may be provided which will better accommodate the vertical and horizontal curves of breast material, and provide support for the underlying breast by the elasticity yielded in three directions, knitted fabric mesh can yield. Secondly, warp knit fabric will not unravel when cut in the operating room by the surgeon as will woven mesh. Knitting machines and their function and the intertwined material yielded therefrom which won't run or ravel when cut, such as warp knit and stitches affecting the shape and elasticity such as knit, purl, cast on, cast off are well known in the art, as are weaving machines which employ warp and fill fibers to form material, and such need not be overly described herein.

This ability not to easily unravel is a particular improvement over the currently employed conventional woven mesh fabric, which even if heated to help maintain thread engagement, will unravel along unfinished edges when cut, and even when not cut. If this woven fabric is cut on a diagonal line to the perpendicular woven threads, unraveling is particularly acute, and the fabric on the diagonal will over stretch under tugging force. This unraveling and over stretching is a nightmare for a surgeon customizing a planar woven sheet the operating room which is remedied by the use of knitted fabric herein described as a particularly preferred mode of the device.

With regard to biocompatibility the mesh material herein is mated with a layer of titanium. Titanium further has the inherent property to osseointegrate, wherein there is direct structural and functional connection between living bone and the surface of the titanium making it further desirous for medical use in implants and the like. Titanium is additionally non-ferromagnetic, making it less likely to interfere with imaging during subsequent conventional MRI technology when combined with the underlying thread or yarn of the knitted mesh.

However, in most cases, titanium coatings or layers must be deposited for adherence at high temperatures which would melt the underlying synthetic fabric yarn forming the mesh scrim provided by such materials for example, polypropylene or polyethylene or other woven or knitted polymeric fabric formed to thread or yarn to be suitable for use in knitting or weaving a mesh structure.

As such, there is a continuing unmet need for an improved medical mesh implant material especially for use to support non planar body tissue having three dimensional curves such as the breast. Such a material should provide enhanced bio-compatibility with surrounding body tissue, to alleviate the infection and rejection problems of current implant fabrics through the provision of a titanium layer on the surface of the material which contacts the patient's flesh.

However, the placement of the metallic titanium coating on the contact surface of the thread or yarn forming the knitted or woven mesh should be engaged in a fashion so as to not melt, or to stiffen the supple nature of the underlying woven or knitted polymeric yarn or thread material. Further, such an implantable fabric should be formed in a manner to provide the surgeon with predictable support, as well as predictable elasticity of the formed mesh sheet, even when employed in a curved surface, through weaving or most preferably knitting the initially planar mesh in a manner that provides vertical support to hold the tissue or implant and thereby resist sagging, but, allow lateral and diagonal elasticity to accommodate the curved and arched nature of the formed breast and thereby provide a more natural appearance and movement such as while walking, to the patient's breasts once implanted.

Further, such a mesh fabric should be providable in a kit of a plurality of individual mesh pieces, each of varying sizes of mesh swatches, which can either be employed as-is due to the chosen customized size, or cut to dimensions for easy implantation with little or no trimming and without unraveling once so cut. Finally, such an implantable mesh should ideally provide a visual aid, which when viewed by a user such as a physician, to cut the implant mesh along predictable lines should it need it, to form the desired dimensions, which allow a surgeon to obtain an even arc or curve of the fabric engaged with a breast, once cut, but to concurrently limit folding and kinking and unraveling and thereby provide the most correct fit for a patient as needed.

The forgoing examples of related art and limitation related therewith are intended to be illustrative and not exclusive, and they do not imply any limitations on the invention described and claimed herein. Various limitations of the related art will become apparent to those skilled in the art upon a reading and understanding of the specification below and the accompanying drawings.

SUMMARY OF THE INVENTION

The device herein disclosed and described provides a solution to the shortcomings in prior art of implantable meshes for breast implant support and augmentation, and other organ or tissue support. The disclosed implantable fabric mesh, achieves the above noted goals, through the provision of a woven or preferably knitted, medical mesh implant device, with a thin and flexible bio-compatible layer of material on the exterior of the yarn or thread or formed mesh, which contacts surrounding tissue. The preferred biocompatible layer on the thread, yarn, or formed mesh, is a titanium surface layer which is thin enough to not inhibit the elasticity and stretching of the formed yarn, thread, or woven or knitted fabric mesh. Further, the coating or layer of biocompatible material is engaged in a manner to prevent stiffening of the formed underlying mesh structure and thereby provides patients increased tolerance to long term presence when implanted in the body.

Further, as noted, the mesh formed as a knitted fabric in a particularly preferred mode, allows for stretching and elasticity in the length, width, and diagonal lines of the formed mesh swatch. This stretching and elasticity also provides three dimensional support to the curved tissue of a breast supported by the knitted mesh material which significantly enhances the performance of mesh supports to curved tissue such as breast tissue thereby yielding a more natural appearance and movement during movement such as walking by the patient.

In accordance with a first particularly preferred mode, the implantable fabric is knitted using conventional knitting machines, from a synthetic or other polymeric material formed into a single or multi-strand filament or strand or yarn. Such material forming the filament may be one or a combination of synthetic materials including polypropylene, polystyrene, polyester, polynosic rayon, or other suitable synthetic material for use to form a knitted or woven mesh.

The yarn or filament forming the mesh, ether before knitting or weaving, or once formed into a mesh structure, is coated or otherwise has imparted to the exterior surfaces of the strands, a covalently bonded titanium surface coating. Other means which do not melt the yarn and achieve a non-migrating attachment of the titanium may be used and are anticipated. However, the current favored mode of attachment of the titanium is accomplished using a chemical vapor deposition (CVD) of the titanium onto the underlying thread, yarn, or formed mesh material thereby achieving a strong bond of titanium directly with the exterior surface of the material of the underlying device. The formed bond with the thread, yarn, or filament forming the mesh, is substantially a unitary structure of titanized polymeric material with the titanium covering substantially the entire exposed surface of the fabric mesh which contacts patient tissue. This process involves the titaniumization of the polymeric material forming mesh at low temperatures under 165 degrees centigrade, using a special plasma-coating process known as PACVD (plasma-activated chemical vapor deposition).

Other preferred means of coating can include chemical vapor deposition (CVD) and plasma-activated chemical vapor deposition (PACVD) when performed at a temperature less than the melting temperature of the synthetic fiber forming the yarn, thread, or filament formed to the knitted or woven mesh.

Titanium deposited to the fabric surface in this fashion will not migrate one the mesh is implanted, and will elicit little to no immune system response of the mesh with surrounding tissue, and generally does not have toxic or other injurious effects on the body. Thus the implanted mesh can be left in the body without discomfort, infection, or irritation caused by conventional meshes which in recent years have shown to cause infection and rejection.

Further, titanium employed in thin layers on the exterior surface of the yarn, thread, or filament forming the mesh structure, is bonded in an ultra thin layer currently between 15-75 nm. Formed to this range, once bonded, the titanium will itself stretch and thus does little to effect any normal flexibility of the underlying mesh as is needed to form the three dimensional curvature of the supported breast and will stretch if the fabric stretches. Further utility is found in that titanium has anti-thrombogenic quality to prevent the formation of blood clots which have recently been found to form with conventional woven support mesh fabric.

It is noted that the mesh device herein may instead be woven or knitted to form the mesh scrim for the titanium layer. Currently a knitted fabric is preferred because knitted fabric, especially after titanium coating, will not unravel if cut by the surgeon. However, if the titanium coating is adhered to the fabric mesh which is woven, or knitted, it provides a means to prevent woven fabric from unraveling and stray threads coming loose from the weave by covering around the overlying and underlying threads, yarn, or filament of the weave and holding them in a bond to each other. The titanium layer on knitted fabric enhances the fabric mesh's ability to resist unraveling. This is important since the physician may be required to cut or trim portions of the mesh structure to properly fit the many different breast sizes of a patient where an unraveling at the edges can cause many problems.

As noted, in another particularly preferred mode of the device, the synthetic material is coated or otherwise formed with an exterior layer of titanium upon the yarn, thread, or filament, prior to it being woven or knitted into the resulting mesh structure herein. This will insure that the overlapping surfaces of the filaments, yarns, or threads, forming the structure, are coated with titanium which may not be the case when coating after forming the mesh structure. Thus any such area contacting tissue of the patient will contact the titanium interface.

For convenience sake, the various terms such as yarn, filament, thread, monofilament, and the like, which speak of linear threads which are woven or knitted to fabric mesh, are herein called filament. However no limitation of the linear material should be assumed and the use of the term filament is simply for convenience.

In accordance with the above noted preferred modes of the invention, the mesh forming the device herein preferably employs a filament thickness (diameter) in the range of 50-100 μm, however other thicknesses suitable for the intended purpose may be employed, which provide suitable support yet maintains flexibility where and in the direction needed. Further the layer thickness of titanium is preferably of a layer thickness in the range of 15-75 nm, again however other thicknesses suitable for the intended purpose may be employed.

In yet another particularly preferred mode of the invention, means for biocompatibility of the device can be provided by forming the mesh device from filament or monofilament composed of titanium wire or multi-strand twisted titanium filament. This mode of the mesh device yields a mesh device formed entirely out of biocompatible material and may further incorporate the strength and resilience characteristics of the titanium metal. In a knitted configuration which as noted will elongated or stretch in multiple directions but not unravel, the formed mesh would provide excellent three dimensional support to the multi directional curves of a human breast. However, it is still within the scope of the present invention to employing a more flexible titanium or titanium alloy known in the art either as coating or filament.

In accordance with at least one preferred mode of the device, the mesh device may be provided to users as a flat sheet of material either substantially rectangular or in a preformed perimeter shape. As such, during use the surgeon or other qualified professional may be required to cut the material to the desired shape and dimensions.

For employment for support in breast reconstructive surgery, the device may be provided as a flat sheet which is especially well suited to form fit and support the horizontal, vertical and diagonal curved lines in the lower curved portion of the breast implant which supports the descending top portion of the breast implant. The device will then be sutured or otherwise engaged about its peripheral edge around the breast implant material to cup or otherwise support the material in a bra-like fashion.

The device in this mode and described in more detail below, especially if of knitted fabric mesh, provides a shape and configuration providing the most support when in curved in a supportive engagement with the implant. This support is a significant improvement in the art and unlike conventional rectangular sheets which the physician must cut employing trial by error to achieve the best form-fitting shape.

To aid the user in cutting the material to various sizes, the provided sheet may include a series of concentric stencil lines which define decreasing surface area size portions of the sheet. The lines preferably will run parallel to the terminating edge of the sheet, to ensure the curvature or other form of a cut edge is maintained in the curve of the original edge. In addition, the stencil lines are preferably formed from bio-absorbable ink or dye which inhibits any immune response by the body. These lines provide the surgeon a target for cutting edges to size the mesh sheet to their patient and be assured of maintaining the curved edges.

In yet another mode of the invention, the mesh device may be provided in a kit of mesh pieces, with each of the plurality of mesh pieces in the kit being of varying sizes (sizes may include small, medium, large, etc, or may conform to well known bra sizes). As such the user, such as a surgeon, rather than having only one option which requires cutting and curving, will not be required to cut any portion of the mesh sheet to fit, and only needs to obtain the pre-sized sheet of the proper size to the intended patient. However, the user may trim portions of the device as needed and if curved lines are provided as targets for cutting this is made easier.

In still yet another mode of the invention employed in breast reconstructive surgery, the mesh device may be provided preformed in a unitary structure without sewing to a substantially hemispherical or cone shape. This may be accomplished by knitting the implant sheet, to yield an arced shaped implant sheet with a finished perimeter edge, using a predetermined depth or arc which corresponds to the natural shapes of breasts. In this mode the device may be formed in a unitary knitted structure, to cover either a portion of the breast implant or the entire breast as needed for support. This mode of the invention will provide a mesh implant which is highly form fitting and thus desirable. Further, because it is knitted such that it will be formed as half or less of a globe with arced threads running in both directions which terminate at a finished non-raveling edge which may be sutured easily or stapled into place. Such a finished edge is not provided in conventional mesh fabric and cutting such conventional fabric increases the convention fabric sheets propensity to unravel and be rendered useless, or problematic for the surgeon who must somehow engage an unraveling edge, with a securement.

Additionally, the material may be knitted to the formed half globe shape, using yarn or filament running one direction that if formed to knit patterns or of material which stretches very little if at all, and an interlacing or yarn running the other direction which provides some desired elasticity to the sheet in that direction. The formed implant sheet thus can be placed in the patient, in a registered engagement, using the printed lines, such that the yarn, filament, or weave, which support the curved breast tissue vertically, has little or no elasticity, which provides an excellent means for long term support against the forces of gravity and impact from walking and running.

Using a filament, yarn, thread, or a knitting pattern which allows elasticity in the horizontal direction, lets the formed mesh material stretch to accommodate the curve of the implant or underlying tissue in a more natural, and comfortable fashion for the patient. Thus the patent and surgeon have long term dependable vertical support of the breast to avoid sagging and other problems, but horizontal elasticity to allow natural feel and movement while supporting the underlying breast tissue or implant.

As noted, using a knitting machine and the proper knitting pattern, and/or yarn or thread material, the implant can be knitted and formed in a single unitary structure requiring no sewing or cutting, to achieve a half-globe or similar shape. Further, the perimeter edge in a knitting may be finished in the process such that it is reinforced to allow for easy suturing which is a significant enhancement over conventional unraveling cut or other edges. As noted, marks may be stenciled on the formed implant as targets for positioning to aid the surgeon in proper positioning relative to the breast, to place the vertical threads or knitted-weave in the proper alignment to support the breast or implant and the horizontal elastic knitted-weave in the proper orientation to provide elasticity for comfort and natural appearance.

Further, in either the half globe or conical mode, or the planar mode of the implant material, the finished piece may include the provision of stencil lines, formed of bio-compatible ink or die, as noted above to allow the user to customize the shape and form but achieve even arcs and cuts to avoid problems uneven cuts can cause such as folds and unnatural appearance. It is also within the scope of the invention that this mode may additionally be provided in a kit of different sized mesh implants wherein the user only needs to obtain the pre-sized mesh structure of the proper size, and simply suture or staple it in place.

With regard to the directional stretch and support mode of the implant device, in the art of breast reconstructive surgery, prosthetic implants are often expanded over intervals of time to gently stretch the overlying skin to the desired size, shape and form. As such, by providing a horizontally stretchable mesh implant device, the vertical support provided by the mesh device can be maintained throughout the expanding process without chance of rupture or miss-formation of the implant/mesh. Further, even if implant expansion is not desired, the underlying directional elasticity of the mesh implant can better allow the breast and implant material to move in a natural manner which is comfortable to the patient.

In a particularly preferred mode, the mesh implant structure may be formed using thread or knitting or weaving patterns or both, to allow for an elongation in the range of 0-30% in the horizontal axis, 0-30% in the vertical axis. However, it must be noted that it is within the scope of the invention that other ranges of elongation may be employed which are suitable for the intended purpose, and are anticipated. In this mode it is additionally preferred that the device include markings to register the orientation as needed to properly align the device in the as used mode.

The device herein provides an improved medical mesh implant device which is well adapted for employment with breast reconstructive surgery. However it is noted that the provisions of the present invention may additionally deem suitable for employment with hernia repair or any other procedure one skilled in the art may readily recognize, and is anticipated.

With respect to the above description, before explaining at least one preferred embodiment of the herein disclosed invention in detail, it is to be understood that the invention is not limited in its application to the details of construction and to the arrangement of the components in the following description or illustrated in the drawings. The invention herein described is capable of other embodiments and of being practiced and carried out in various ways which will be obvious to those skilled in the art. Also, it is to be understood that the phraseology and terminology employed herein are for the purpose of description and should not be regarded as limiting.

As such, those skilled in the art will appreciate that the conception upon which this disclosure is based may readily be utilized as a basis for designing of other structures, methods and systems for carrying out the several purposes of the present disclosed device. It is important, therefore, that the claims be regarded as including such equivalent construction and methodology insofar as they do not depart from the spirit and scope of the present invention.

As used in the claims to describe the various inventive aspects and embodiments, "comprising" means including, but not limited to, whatever follows the word "comprising". Thus, use of the term "comprising" indicates that the listed elements are required or mandatory, but that other elements are optional and may or may not be present.

It is an object of the invention to provide a mesh implant device being formed from a synthetic material filament such as a polymeric material, which is additionally imparted or otherwise formed with a bonded layer of titanium on the exterior surface which contacts patient tissue providing a means for bio-compatibility of the device.

It is another object of the invention to provide a mesh implant device which is formed form a monofilament titanium wire or multi-strand twisted titanium yarn to also provide a means for bio-compatibility of the device.

It is another object of the invention to provide a knitted mesh implanted device which provides superior stretching and conforming support to the curved tissue of a breast and has finished edges which won't unravel.

It is yet another object of the invention to provide a woven mesh implant device.

It is an object of the invention to provide a mesh implant device with is suitable formed to support a breast implant.

It is still another object of the invention to provide a mesh implant device including stencil markings which correspond to various sizes and dimensions and provide a means for cutting and/or means for positioning of the mesh implant relative to the breast tissue.

It is yet another object of the invention to provide a mesh implant device including markings to register the horizontal or vertical disposition of the device to match the direction of support and elasticity with the proper position in the patient.

It is still yet another object of the invention to provide a mesh implant device with determined elasticity in one or both of the horizontal and vertical directions.

It is an object of the invention to provide a mesh implant device which is providable in a kit of varying sizes and dimensions.

These and other objects features, and advantages of the present invention, as well as the advantages thereof over existing prior art, which will become apparent from the description to follow, are accomplished by the improvements described in this specification and hereinafter described in the following detailed description which fully discloses the invention, but should not be considered as placing limitations thereon.

BRIEF DESCRIPTION OF DRAWING FIGURES

The accompanying drawings, which are incorporated herein and form a part of the specification, illustrate some, but not the only or exclusive, examples of embodiments and/or features. It is intended that the embodiments and figures disclosed herein are to be considered illustrative rather than limiting. In the drawings.

DETAILED DESCRIPTION OF THE PREFERRED EMBODIMENTS OF THE INVENTION

Figures 1, 1A, 1B, 2, 3, 4:
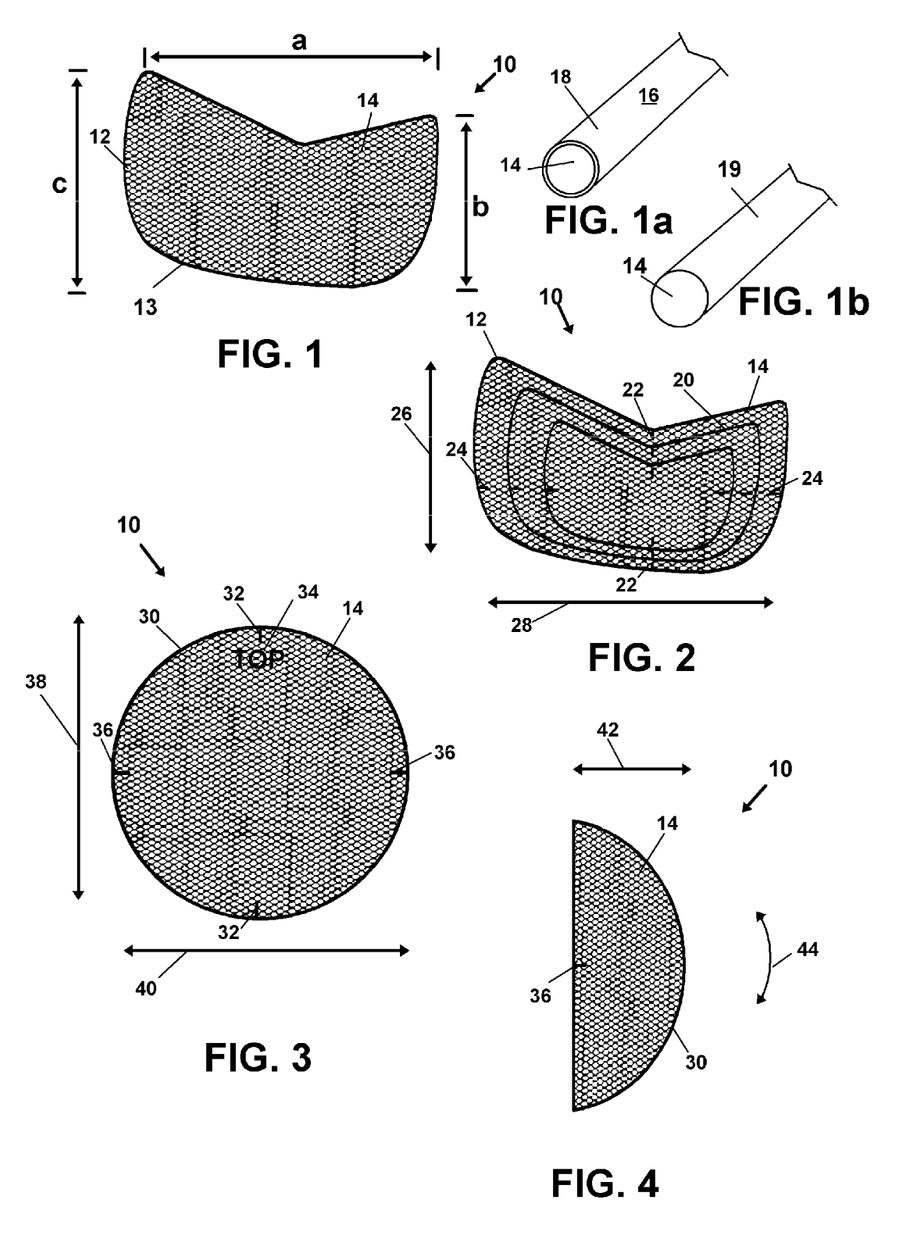
FIG. 1 shows a front view of a first particularly preferred mode of the device shaped to cup or otherwise engaged a breast implant or breast tissue, in a bra-like supporting fashion, which is a flat sheet of mesh knitted from synthetic filament having a titanium surface layer.
FIG. 1a shows a cross sectional view of the preferred synthetic filament mesh having a titanium surface layer bonded to the underlying polymeric or other synthetic material forming the filaments of the weave or knit.
FIG. 1b shows a cross sectional view of a preferred filament formed from synthetic material or entirely from monofilament titanium wire.
FIG. 2 is a front view of another particularly preferred mode of the device employing a plurality of stencil marking which provided a means for the user to cut along and to form smaller sized mesh implants of the same shape, there is additionally shown registration markings which may be employed by themselves, to allow the surgeon to register the vertical and horizontal dispositions of the knit or weave, for best support of the breast, during implantation.
FIG. 3 is a front view of yet another particularly preferred mode of the device intended to engage substantially over the entirety of an implant, and formed in a unitary structure into cone or hemispherical configuration, by knitting, also having direction registration markings disposed thereon.
FIG. 4 is a side view of the mode of the device of FIG. 3 detailed the prescribed arc length and depth of the formed mesh fabric device which can be modified to obtain desired geometric characteristics and can be formed in a unitary structure using a knitting machine.

Now referring to drawings in FIGS. 1-9, wherein similar components are identified by like reference numerals, there is seen in FIG. 1 a view of the first particularly preferred mode of the device 10 being a substantially flat sheet 12 of woven or preferably knitted mesh material, and having an exterior coating or surface providing means for biocompatibility with contacting surrounding tissue. Due to the customization in elasticity, shape, and finished non raveling edges, provided by formation of the device 10 on knitting machines, one mode of the device 10 is preferably knitted from a polymeric or other synthetic yarn, thread, filament, or mono-filament 14 (FIG. 1a) or a twisted multi filament. It must be noted that the device 10 may alternatively be woven into the mesh structure shown and with the biocompatible coating would still yield a significant enhancement in supportive implanted meshes.

A knitted formation of the mesh structure, known as a warp knit, provides a means for preventing unraveling of the intertwined filaments 14 forming the mesh, when the mesh fabric is cut. Without the biocompatible coating, such a knitted mesh material alone, formed to smaller and larger knit, and to the curved and different shapes matching that of breast material to be supported, all with finished edges which do not ravel if cut, yield a significant enhancement in the art of supporting mesh material implants. The knitted fabric mesh so formed is further enhanced with the exterior biocompatible material surface imparted to the formed mesh to hold the traversing threads in position as can be done with woven fabric also.

In use, described in more detail shortly, the user may be required to trim or otherwise cut portions of the sheet 12, wherein a knitted structure provides a means to prevent unraveling when cut and is preferred. Further, for modes of the device 10 where cutting or trimming are not required, it is preferred that the edges of the sheet 12 are laser cut to provide a rounded edge. However other means to prevent unraveling may be employed, and are anticipated.

The asymmetrical shape of the mesh sheet 12, defined by the perimeter edge 13 as shown, has been experimentally shown to be especially well suited to engage over the lower or bottom curve portion of a breast implant in a manner to cup or otherwise support the implant in a bra-like fashion. The size of the sheet 12 is generally defined by the dimension of the width 'a', first height 'b' of the edge 13, and second height 'c' of the edge 13. In a preferred kit mode of the device 10, it is preferred that the device 10 be providable in a kit 52 (FIG. 9) of varying sizes of which the physician can suitably select the appropriate size. For example, 'small' size can be defined wherein the width 'a' is in the range of 185-205 mm, height 'b' is in the range of 85-105 mm, and height 'c' is in the range of 110-130 mm; 'medium' can be designated wherein 'a' is in the range of 205-225 mm, 'b' is in the range of 105-125 mm, and 'c' is in the range of 130-150 mm; 'large' can be defined wherein 'a' is in the range of 225-245 mm, 'b' is in the range of 125-145 mm, and 'c' is in the range of 150-170 mm. It is noted that values outside the above noted ranges which a physician deems suitable for the intended purpose may also be employed and are anticipated.

Once the device 10 is in position within the surgical site, the device 10 is engaged by fixing the sheet 12 to the caudal and lateral end of the pectoral muscle with a continuous suture or staple. The lower portion of the device 10 is then stitched to the infra-mammary fold with single stitches. However, the device 10 can be stapled, or otherwise secured to the surrounding tissue by any other means known in the art. It must be noted that the sheet 12 currently shown when simply reversed, is then suitable for support of an implant on the other breast. It is further noted that the device 10 however may be formed to other shapes or dimensions as is within the intended scope of the invention which will become more apparent upon further disclosure, and is anticipated.

In this and following descriptions, the directional prepositions of up, upwardly, down, downwardly, front, back, top, upper, bottom, lower, left, right and other such terms refer to the device as it is oriented and appears in the drawings and are used for convenience only; the terms are not intended to be limiting or to imply that the device 10 has to be used or positioned in any particular orientation.

FIG. 1a shows a cross sectional view of the particularly preferred synthetic monofilament 14, such as polypropylene, polystyrene having an exterior surface 16 layer where a titanium layer 18 is bonded to the underlying polymeric material providing a means for biocompatibility of the device 10. In a preferred mode, the filament 14 is formed with a titanium layer 18 by a process called plasma-activated chemical vapor deposition which produces a strong bond at low temperatures so as not to melt or deform the underlying polymeric material. In the process, gaseous titanium is introduced into the coating chamber as a precursor. By adding energy in form of plasma, the precursor is split into ionized titanium atoms having free electrons on their surface, while additionally exciting the surfaces of the filament 14 which result in their surfaces also having free electrons. The ionized titanium atoms contact the ionized filament surface resulting in the formation of covalent bonds with the free electrons.

Covalent bonds are considered the strongest of chemical bonds thus the titanium is nearly permanently bonded to the synthetic filament 14. In a preferred mode the coating 18 thickness of titanium bonded to the underlying polymeric material is within the range of 15-75 nm, however other ranges suitable for the intended purpose may be employed, and are anticipated. The thin layer of titanium creates a composite filament material which is highly bio-compatible and flexible. It is noted that the formation of the titanium layer 18 can be accomplished either before or after knitting or weaving the filament 14 into the mesh structure.

In another mode of the device 10, shown in FIG. 1b, the filament 14 may instead be a monofilament titanium wire 19 or multi-strand titanium yarn. Such a wire or yarn would be extruded with very short diameters in a manner which can similarly be formed into a knitted or woven mesh structure, and is thus anticipated within the scope of the invention where the bonded layer of titanium may not be desirable.

FIG. 2 shows a view of yet another particularly preferred mode of the device 10. As is shown, this current mode of the device 10 includes the formed mesh sheet 12 including concentric stencil lines 20 defining varying sizes achievable by cutting of the sheet 12. The sheet 12 may be initially provided as the 'large' size noted above, or larger if needed, wherein the successive stencil lines 20 corresponding to smaller sizes. The physician or other qualified professional can employ the stencil lines 20 as an aid to evenly trim or otherwise reform the sheet 12 to another size as needed without the worry of cutting the wrong arc or angle along the edge.

It is preferred that the lines 20 are formed of a bio-absorbable ink or dye which is imparted onto the surface of the sheet 12. Again, in accordance with the kit mode shown in FIG. 9, the device 10 of the current mode may also be providable in the kit 52 comprising one or a plurality of these universal sized sheets 12 each of which have stencil cut lines 20 wherein the users customizes the size and shape per patient.

Further, as noted previously, in accordance with all preferred modes of the device 10, the disclosed mesh invention can provide additional form fitting means by providing a knitted sheet 12 of the mesh which allows for an elongation, or stretching, along the horizontal axis 28, vertical axis 26, or combination thereof into a unitary three dimensional structure. By knitting on a computerized knitting machine, or otherwise forming the mesh sheet 12, to allow for elongation along one or both of the horizontal and vertical axes 28,26, a three dimensional form fitting component can be obtained which is properly sized in arc, form, shape, and volume to accommodate the underlying implant or breast tissue.

As noted previously, prosthetic implants are often expanded over intervals of time to gently stretch the overlying skin to the desired size, shape, fit, and form. As such, by providing a stretchable or elastic mesh implant device 10, the support provided by the mesh device 10 can be maintained throughout the expanding process. Further, the underlying stretchability of the mesh implant can better allow the breast and implant material to move in a natural manner which is comfortable to the patient.

In a particularly preferred mode, the knitted structure of the sheet 12 may be formed to allow for an elongation in the range of 0-30% in the horizontal axis 28 and 0-10% in the vertical axis 26. This provides for excellent support of the tissue or implant vertically against gravity and the force of landing while running or walking. The calculated horizontal elasticity makes the implant more comfortable and allows the breast to appear and feel more natural.

However, it must be noted that it is within the scope of the invention that other ranges of elongation may be employed which are suitable for the intended purpose, and are anticipated. In this mode it is additionally preferred that the device also include vertical registration markings 22 and horizontal registration markings 24 to provide a means for the user or surgeon to register the orientation of the implant as needed to properly align the device 10 in the as used-mode before suturing or otherwise engaging to the patient.

FIG. 3 and FIG. 4 show front and side views respectively of yet another particularly preferred mode of the device 10 formed substantially as hemispherical cup or conical mesh structure 30 (similar to the cup of a bra). In this mode the device 10 may be formed to cover either a portion of the breast implant or the entire implant as needed for support. In this mode the size and shape of the structure 30 is defined by a height 38, width 40, depth 42, and arc length 44 which can be selectively adjusted to the natural shapes of breasts.

It is additionally preferred that this mode of the device 10 may also be providable in the kit 52 (FIG. 9) having a plurality of varying sizes wherein the physician can selectively choose from. As an example, a portion of the kit 52 can include a plurality of mesh structures 30 wherein the height 38 and width 40 are fixed, however the depth 42 and arc length 44 vary along a range; or the depth 42 and arc length 44 are fixed, and the height 38 and width 40 vary along a predetermined range; or any other combination thereof. Thus this mode of the invention will provide a kit 52 of the mesh device 10 which is highly form fitting and thus desirable. Further, it is noted this mode may include the provision of stencil lines as noted above to aid the user to trim or otherwise customize the shape, size, and form.

Still further, it is particularly preferred that this mode of the device 10 be formed as a unitary structure by knitting or otherwise forming the mesh structure 30 as a unit to form an even implant with no stitching, darts, or joints that effect the look or comfort once implanted. Further, in the formation the knitting formation or the material forming the mesh may be adjusted to allow for elongation along one or both of the horizontal and vertical axes as noted above. Therefor this mode also preferably includes vertical registration markings 32 and horizontal registration markings 36 as well as an orientation marking 34 to provide a means to register the orientation as needed to properly align the device 10 in the as used mode.

Figures 5, 6, 7, 8:
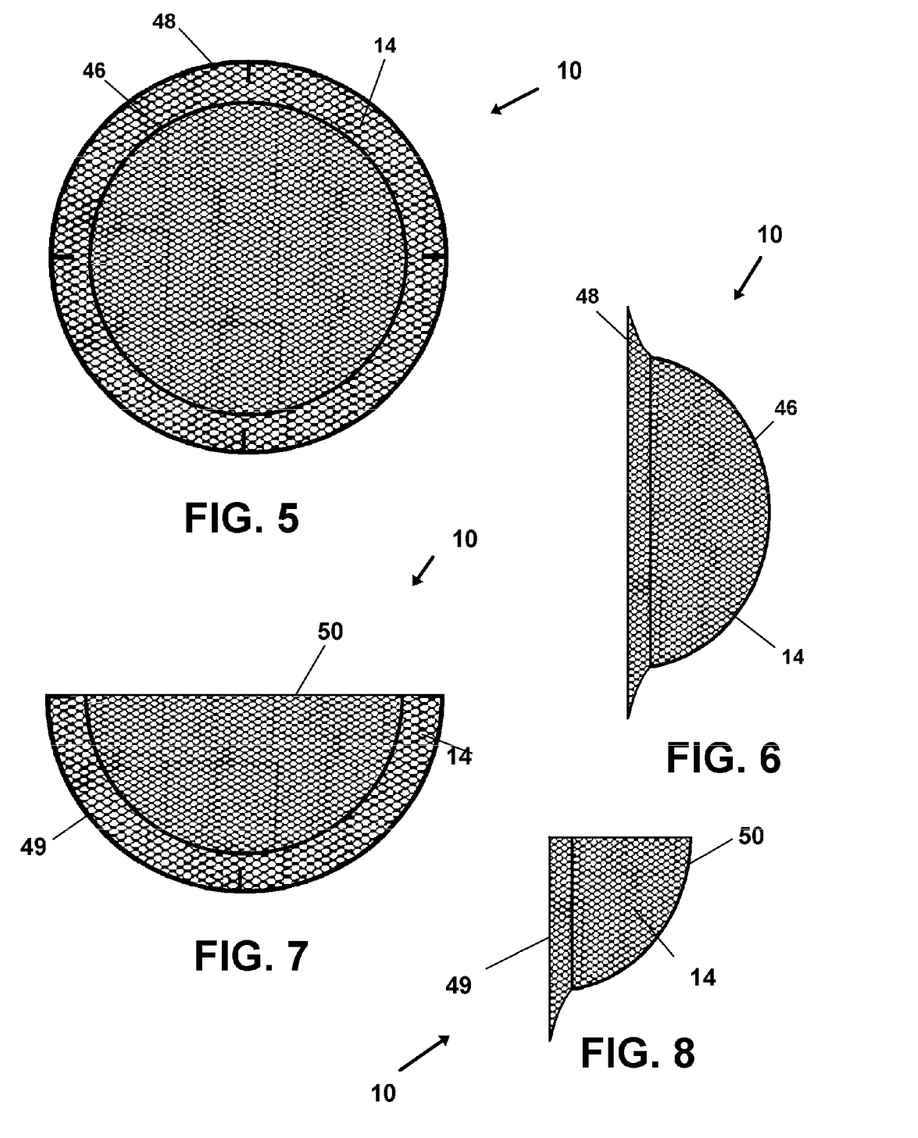
FIG. 5 shows yet another mode of the device which includes a formed cone or hemispherical portion and surrounding flange or lip portion which can be employed for securing the device to the surrounding breast tissue.
FIG. 6 shows a side view of the mode of the device of FIG. 5.
FIG. 7 shows yet another mode of the device which includes a formed half cone or half hemispherical portion and surrounding flange or lip portion which can be employed for securing the device to the surrounding breast tissue.
FIG. 8 shows a side view of the mode of the device of FIG. 7.

FIG. 5 and FIG. 6 show front and side views respectively of yet another particularly preferred mode of the device 10 formed having a substantially hemispherical cup or cone mesh structure 46 and a peripheral flange or lip portion 48 communicating thereabout. In this mode the device 10 may also be formed to cover either a portion of the breast implant or the entire implant as needed for support. For partial coverage, FIG. 7 and FIG. 8 show front and side views respectively of still yet another particularly preferred mode of the device 10 formed having a substantially half hemispherical cup or half cone mesh structure 50 and a peripheral flange or lip portion 49 communicating thereabout.

As is advantage over prior preferred modes, the flange of lip portion 48, 49 provided in the current modes can aid in engaging the device 10 about the surrounding breast tissue by providing increased surface area, when in the engaged as used position.

Figure 9:
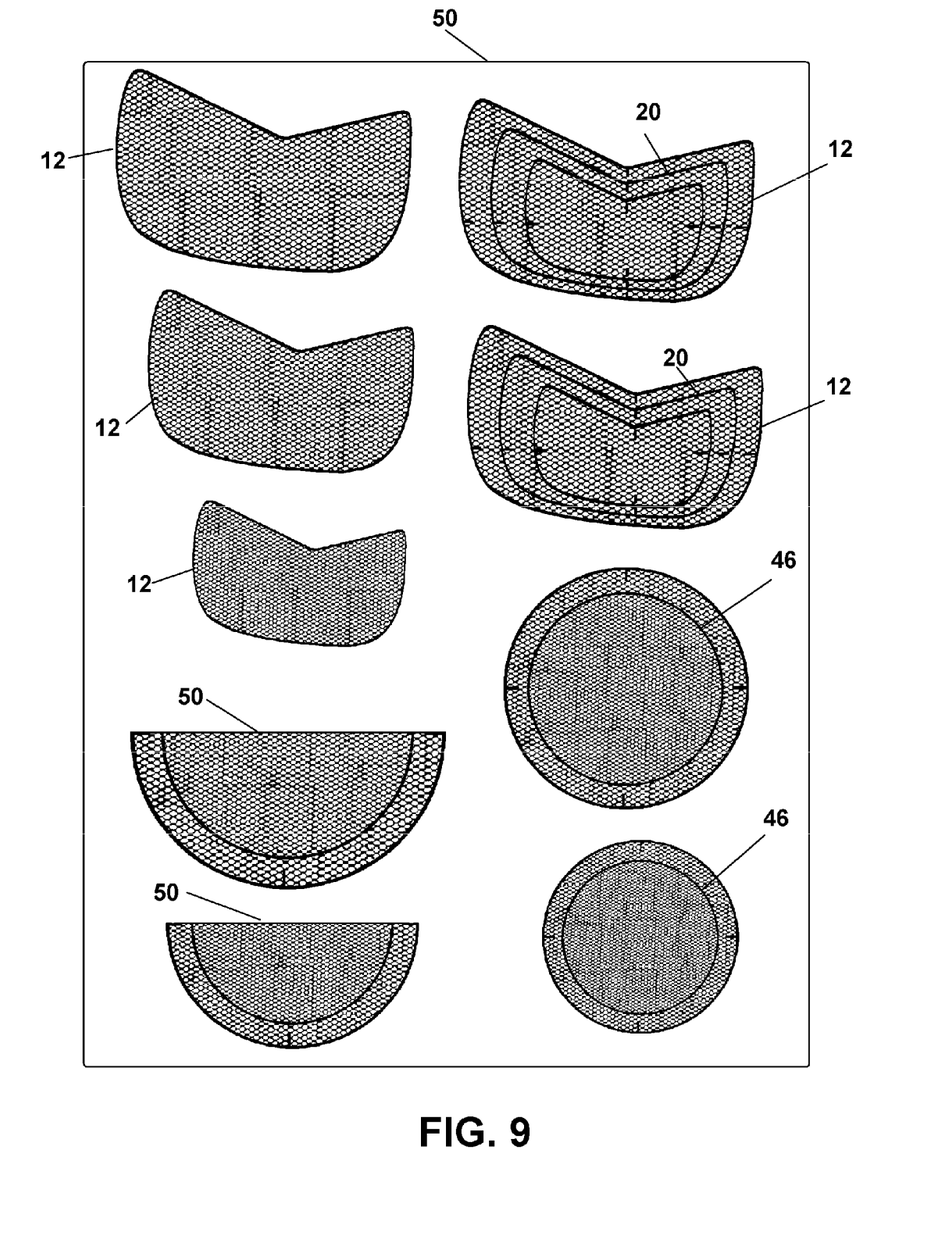
FIG. 9 shows a kit mode of the device provided as a kit having a plurality of mesh implants, providable to the user to allow the user to select the desired device as needed.

Varying sizes, shapes, and geometries of the modes of the device 10 in FIGS. 5-8 may also be providable to the user in the kit mode as shown in the kit 52 in FIG. 9.

The device 10 herein disclosed and described provides an improved medical mesh implant device which is well adapted for employment with breast reconstructive surgery. The provisions and inherent advantages of the device however may additionally deem suitable for employment with hernia repair or any other procedure one skilled in the art may readily recognize, and is anticipated.

While all of the fundamental characteristics and features of the invention have been shown and described herein, with reference to particular embodiments thereof, a latitude of modification, various changes and substitutions are intended in the foregoing disclosure and it will be apparent that in some instances, some features of the invention may be employed without a corresponding use of other features without departing from the scope of the invention as set forth. It should also be understood that various substitutions, modifications, and variations may be made by those skilled in the art without departing from the spirit or scope of the invention. Consequently, all such modifications and variations and substitutions are included within the scope of the invention as defined by the following claims.

What is claimed is:

1. A mesh device for supporting one or a combination of a breast implant or breast tissue, when employed in reconstructive surgery comprising:
   a plurality of interlaced filaments forming a mesh structure, said mesh structure having surface area having a shape defined by a perimeter edge, and having a central section within said perimeter edge;
   said filaments having an exterior surface;
   means to prevent an unraveling of said interlaced filaments upon a cutting across said filaments in said central section;
   a series of concentric lines positioned on said mesh structure, said concentric lines running parallel to said perimeter edge of said mesh structure;
   said series of concentric lines defining a decreasing portion of said surface area of said mesh structure; and
   a trimming of said mesh structure along said concentric lines forming a cut edge surrounding said decreasing portion of said surface area which maintains said shape of said mesh structure originally defined by said perimeter edge.

2. The mesh device of claim 1, additionally comprising:
   said series of concentric lines defining a plurality of said decreasing portions;
   a first of said plurality of decreasing portions defined by a said series of concentric lines closest to said perimeter edge; and
   a smallest of said plurality of decreasing portions defined by a said series of concentric lines furthest from said perimeter edge.

3. The mesh device of claim 1 additionally comprising:
   said mesh structure formed with curvature of said central portion, to match and support a curved portion of tissue or a breast implant of a human breast, when operatively positioned adjacent thereto; and
   whereby said mesh structure implanted in a body of a patient provides a curved support for said breast tissue or breast implant.

4. The mesh device of claim 2 additionally comprising:
   said mesh structure formed with curvature of said central portion, to match and support a curved portion of tissue or a breast implant of a human breast, when operatively positioned adjacent thereto; and
   whereby said mesh structure implanted in a body of a patient provides a curved support for said breast tissue or breast implant.

5. The mesh device of claim 1 additionally comprising:
   a covalent bonded coating of titanium upon said interlaced filaments; and
   said covalent bonded coating having a thickness of 15-75 nm.

6. The mesh device of claim 2 additionally comprising:
   a covalent bonded coating of titanium upon said interlaced filaments; and
   said covalent bonded coating having a thickness of 15-75 nm.

7. The mesh device of claim 3 additionally comprising:
   a covalent bonded coating of titanium upon said interlaced filaments; and
   said covalent bonded coating having a thickness of 15-75 nm.

8. The mesh device of claim 4 additionally comprising:
a covalent bonded coating of titanium upon said interlaced filaments; and
said covalent bonded coating having a thickness of 15-75 nm.

9. The mesh device of claim 1 additionally comprising:
vertical registration markings and horizontal registration markings positioned upon said mesh structure, said vertical registration markings and said horizontal registration markings employable to register an orientation said mesh structure during an implantation in a patient.

10. The mesh device of claim 2 additionally comprising:
vertical registration markings and horizontal registration markings positioned upon said mesh structure, said vertical registration markings and said horizontal registration markings employable to register an orientation said mesh structure during an implantation in a patient; and
said coating forming a biocompatible interface between said interlaced filaments, and body tissue placed in a contact with said mesh device.

11. The mesh device of claim 3 additionally comprising:
vertical registration markings and horizontal registration markings positioned upon said mesh structure, said vertical registration markings and said horizontal registration markings employable to register an orientation said mesh structure during an implantation in a patient.

12. The mesh device of claim 6 additionally comprising:
vertical registration markings and horizontal registration markings positioned upon said mesh structure, said vertical registration markings and said horizontal registration markings employable to register an orientation said mesh structure during an implantation in a patient.

13. The mesh device of claim 8 additionally comprising:
vertical registration markings and horizontal registration markings positioned upon said mesh structure, said vertical registration markings and said horizontal registration markings employable to register an orientation said mesh structure during an implantation in a patient.

* * * * *